United States Patent [19]
Roth

[11] Patent Number: 5,215,772
[45] Date of Patent: Jun. 1, 1993

[54] METHOD AND APPARATUS FOR SEPARATING LEAN MEAT FROM FAT

[76] Inventor: Denis E. Roth, 236 Riverton Pl., San Ramon, Calif. 94583

[21] Appl. No.: 834,738

[22] Filed: Feb. 13, 1992

[51] Int. Cl.⁵ .................. B07C 5/00; G01N 33/00
[52] U.S. Cl. .................. 426/231; 209/577; 209/587; 209/922; 426/480
[58] Field of Search ......... 426/231, 480; 209/577, 209/587, 656, 922; 99/489

[56] References Cited

U.S. PATENT DOCUMENTS

| | | | |
|---|---|---|---|
| 2,357,566 | 9/1944 | Walter et al. | 209/173 |
| 2,373,361 | 4/1945 | Walter | 209/587 |
| 3,044,619 | 7/1962 | Knolle | 209/147 |
| 3,312,343 | 4/1967 | Elder et al. | 209/147 |
| 3,489,277 | 1/1970 | Silverman | 209/587 |
| 3,572,503 | 3/1971 | Hezel | 209/920 |
| 3,581,888 | 6/1971 | Kelly et al. | 209/587 |
| 3,930,991 | 1/1976 | Gillespie | 209/580 |
| 3,977,526 | 8/1976 | Gordon et al. | 209/587 |
| 4,122,952 | 10/1978 | Richards | 209/587 |
| 4,201,302 | 5/1980 | Roth | 209/577 |
| 4,513,868 | 4/1985 | Culling et al. | 209/587 |
| 4,624,367 | 11/1986 | Shafer et al. | 209/587 |
| 4,657,144 | 4/1987 | Martin et al. | 209/587 |
| 4,699,273 | 10/1987 | Suggi-Liverani et al. | 209/587 |
| 4,909,930 | 3/1990 | Cole | 209/587 |

FOREIGN PATENT DOCUMENTS

81/03547 12/1981 World Int. Prop. O. .......... 426/231

*Primary Examiner*—George Yeung
*Attorney, Agent, or Firm*—Townsend and Townsend Khourie and Crew

[57] ABSTRACT

Meat having lean meat portions and fat meat portions is cut into relatively small segments of higher lean meat content and higher fat content. The segments are vibrated to prevent clinging between segments as they are conveyed to a segment spacing station where the segments are spaced from one another. The spaced segments are passed through the sensing zone of a sensor where an optical characteristic related to fat or lean meat content is sensed. Segments having a higher lean meat content are separated from segments of higher fat content in response to the sensed characteristic.

28 Claims, 2 Drawing Sheets

METHOD AND APPARATUS FOR SEPARATING LEAN MEAT FROM FAT

BACKGROUND OF THE INVENTION

The present invention relates to separating meat components such as fat and lean meat generally, and more particularly to upgrading trim pieces of meat to a fraction having a higher lean meat content and a fraction having a higher fat content.

Various techniques have been disclosed for dividing fat and lean meat using photoelectric or color sensitive detectors. These techniques are representative of efforts to eliminate problems associated with manual separation of fat and lean portions of meat products. One such technique is disclosed in U.S. Pat. No. 3,930,991 to Gillespie. In Gillespie, a combination of lean and fat meat is first cut into chunks of uniform size and then passed through a photometric sensor for detecting an optical property relating to the lean meat content of the chunks. The chunks are then sorted by a device responsively coupled with the photometric sensor. The individual chunks are preferably maintained at a low temperature close to freezing (which, for meat, is about 26°-32° F.) in order to permit singularizing of the chunks for passage through the photometric sensor. Such requirements significantly reduce the rate of separation in addition to increasing operating costs for the process as discussed in U.S. Pat. No. 4,201,302. Further, it has been observed that meat ground at a temperature below about 40° F. undergoes "fracture" which is due in part to the presence of frozen crystals in the meat at this temperature. This reduces the binding qualities of the meat, as well as the quality of protein in the meat. When meat having reduced binding qualities is used to make bologna or sausage, for example, the end product has an undesirable texture and can fall apart. It has also been observed that product formed by grinding semi-frozen or frozen meat has less distinctive color characteristics than if it were ground from nonfrozen meat (i.e., the red lean portions become lighter in color). Accordingly, detection of lean and fat based on color or light-dark characteristics of the meat product with conventional optical sensing devices becomes more difficult. Meat product that is ground when frozen also has a spongy texture which includes pores that can appear as dark spots to the detection apparatus. An erroneous lean meat reading can result.

U.S. Pat. No. 2,373,361 to Walter also discloses a system using photoelectric detectors for separating fat and lean portions of meat products. In this system, substantial processing is required to condition the individual particles for passage through the photoelectric sensor. Specifically, the fat trimmings are ground up and deposited on a belt. The ground meat is pressed into a thin layer on the belt and then cut into thin ribbons of about ½ to 1 inch in thickness. Light reflected from the ribbons is sensed by a photoelectric cell. Scrapers are operated in accordance with the light detected from the photoelectric cell to scrape lean meat from the belt into a first chute. The fatter portions remain on the belt and are later scraped therefrom into a second chute. The process depends on the grinding of the meat into course particles so that it can be flattened onto the belt and also depends on the stickiness of the meat to adhere to the belt.

U.S. Pat. No. 4,201,302 to Roth discloses separating fat and lean meat by passing the combined fat and lean meat through an extruder sized to form a plurality of generally continuous chains of material. A sensor senses the character of the material along the length of each chain while the meat product material is passed through a tube. A diverter operates in response to the sensor to direct fat exiting the tube toward one collection bin and lean meat exiting the tube toward another collection bin. It has been found that the inner walls of the tubes can become contaminated with lean or fat particles (the meat product material smears on the inner walls of the tubes) which can lead to sensing errors. In addition, the tubing can become fogged over time which can result in erroneous fat readings by the sensing apparatus. Accordingly, the tubes must be continuously cleaned and possibly replaced to maintain sensing accuracies. The complex cutting arrangement for directing the fat and lean portions to the appropriate bin also must be maintained to provide accurate removal of material. It has also been observed that the meat product flow rate from the grinder can vary, thereby interfering with the timing of the diverter or cutting devices.

SUMMARY OF THE INVENTION

The present invention is directed to a method and system for upgrading a particular quantity of trim meat pieces that avoids the problems and disadvantages of the prior art. The invention accomplishes this goal by providing a system for separating selected components of meat products in which meat is extruded and cut to form a plurality of discrete pieces of material. That material is deposited on a vibrating conveyor to prevent the meat pieces from clinging together, while being conveyed from the extruder to a spacing mechanism for spacing the discrete pieces of meat from one another before conveying those pieces along a high-speed conveyor to a sensor. The spacing mechanism comprises the juncture between the vibrating conveyor and the high-speed conveyor. The spaced meat pieces are then passed or projected (by the high-speed conveyor) through a sensing zone where an optical characteristic related to the quantity of lean meat or fat within the meat pieces is detected. The meat pieces having a higher lean meat content are separated from the meat pieces having a lower meat content in response to the sensed characteristic. Since the meat pieces are prevented from sticking to each other, as well as from sticking to components of the preliminary or vibrating conveyor, the meat can be processed at temperatures above freezing and preferably above about 40° F. It has been observed that degradation of the meat is minimized when the meat is extruded and/or cut at temperatures above about 40° F. This enhances the reprocessing value of the end product. In addition, the color distinction between the lean meat and fat is significantly more pronounced at temperatures above freezing as compared to lean and fat maintained below freezing. This color gradient improves sensing accuracies and, thus, separating efficiencies.

The above is a brief description of some deficiencies in the prior art and advantages of the present invention. Other features, advantages and embodiments of the invention will be apparent to those skilled in the art from the following description, accompanying drawings and appended claims.

DESCRIPTION OF THE PREFERRED EMBODIMENT

Figure 1:
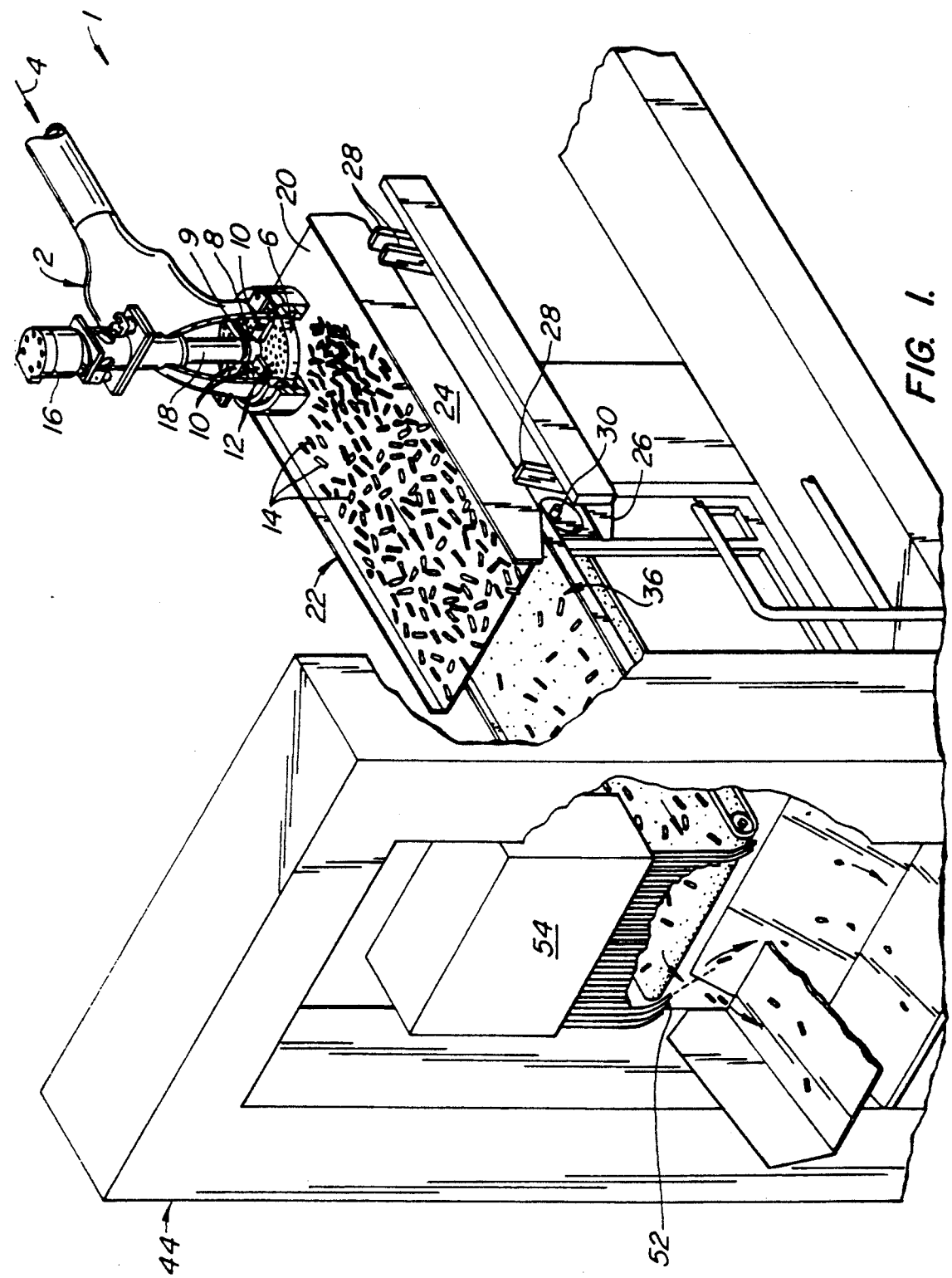
FIG. 1 is a prospective view of the lean-fat separator in accordance with the principles of the present invention.

Referring to the drawings in detail wherein like numerals indicate like elements, lean-fat separator 1 is illustrated in accordance with the principles of the present invention. Although the present invention is described with reference to separating lean and fat components of meat products, it should be understood that the invention can be used for separating other components. For example, the separator can be used to separate bone from fat or lean meat or a combination thereof. The invention also can be used to remove foreign components of meat products such as metal or the like.

Figure 2:
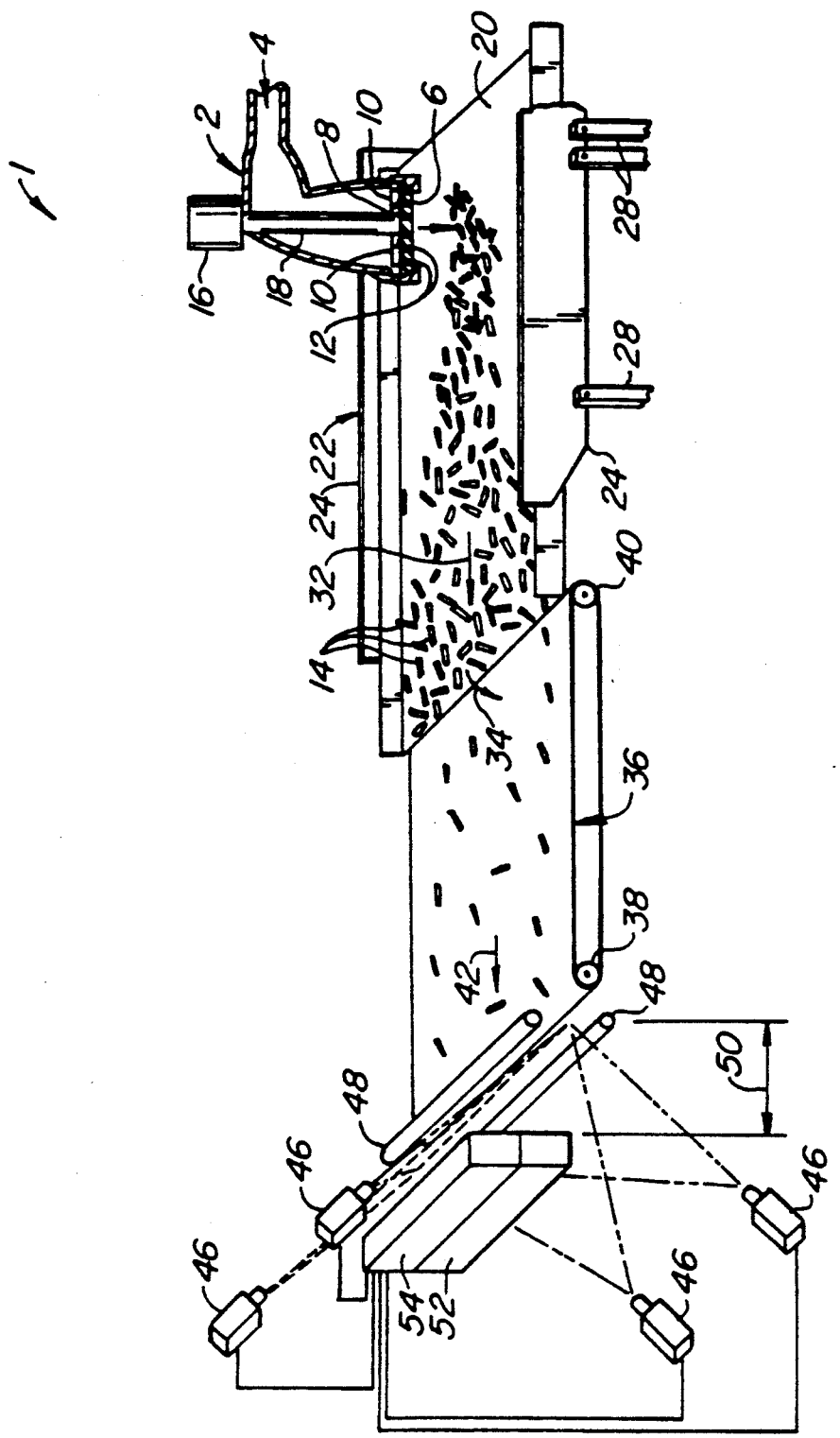
FIG. 2 is a schematic representation of the system illustrated in FIG. 1.

Referring to FIGS. 1 and 2, meat trimmings, which typically have been trimmed from portions of an animal, are fed (as designated by arrow 4) into a grinder, such as grinder 2, in a way conventional to those skilled in the art to extrude and cut the meat into discrete segments. Generally, the trimmings comprise animal fat in large part with a small portion of lean meat. Since the value of the lean meat is substantially greater than the fat, separation of the fat and lean meat is desirable for purposes of economy. Grinder 2 includes a rotating auger (not shown), a replaceable extruder or die plate 6 and a cutting mechanism 8 having a rotating hub 9 and knife blade 10 extending therefrom. The auger separates the meat introduced into the grinder from, for example, a hopper (not shown), and forces it through a plurality of uniformly sized holes or openings 12 formed through extruder plate 6. The extruded meat is cut into meat segments or pieces 14 by rotating hub 9 and knife 10 which blades are rotated by motor 16 through drive shaft 18. One suitable grinder for practicing the present invention is Model 300 VARIKUT ® Grinder/Mincer manufactured by Marlen Research Corporation of Overland Park, Kans.

The separation in the cutting process tends to liberate the fat from the meat, yielding meat segments having a high percentage of lean meat and pieces having a high percentage of fat. Generally, the smaller the segments, the more homogeneous they are in composition. Thus, if the segments could be made small enough, a perfect separation could be accomplished. However, if the segments are made too small, their usefulness in reprocessing, such as in the making of hamburger, is greatly diminished. Segments that are too small will produce a meat product of undesirable consistency (mush) when reground in downstream processing. It has been found that meat segments having a mean diameter in the range of about $\frac{1}{4}$ to 1 inch and a mean length also in the range from about $\frac{1}{4}$ to 1 inch provide desirable results. Optimally, the meat segments are cylindrical and have a length and diameter of about $\frac{1}{2}$ inch. However, the meat pieces can be formed in other shapes without departing from the scope of the invention. In addition, the diameter of extruder openings 12 can be larger than the $\frac{1}{2}$ inch (to form segments with a diameter greater than $\frac{1}{2}$ inch) for some applications, for example, where accurate separation between fat and lean meat is not necessary. In some instances, it is only desired to upgrade the percentage of lean meat, for example, from 10% to 25%. In that case, very large or coarse openings could be provided in the grinder or extruder to permit removal of only a portion of the fat necessary to raise the lean meat percentage to about 25%.

The meat segments are conveyed from grinder 2 to a sensing zone where at least one characteristic of each segment is sensed for sorting the segments based on their composition. However, to properly present the meat segments in the sensing zone, it has been found that each individual segment should be spaced from adjacent segments. To accomplish such spacing, while maintaining the meat at a temperature above freezing, and preferably above about 40° F. to enhance its reprocessing value and maximize separating efficiencies as discussed above, the meat segments are first gravitationally fed directly from grinder 2 to vibrating tray 20 of a conventional vibrating conveyor, such as vibrating conveyor 22, from which they are transferred to a high-speed conveyor. Vibrating tray 20 is secured to conveyor side walls 24 which are coupled to frame 26 through resilient mounting plates 28. A vibratory motor 30 drives tray 20 in a rapid reciprocatory manner to vibrate the tray. In this way, the segments are distributed along the width of the conveyor and moved therealong as designated by arrow 32 to high-speed conveyor 34, while clinging between individual segments is prevented.

The meat segments fall under the influence of gravity as designated by arrow 34 (FIG. 2) from vibrating conveyor 22 onto high-speed (endless belt) conveyor 36 which is trained conventionally around pulley wheels 38 and 40. The width of conveyor 36 is at least about three to six feet and preferably about fifty-four inches. High-speed conveyor 36 operates at a speed of about 500 to 600 feet per minute for purposes of productivity and spacing as discussed hereafter. The meat segments travelling at a relatively slow speed of about 3-4 feet per minute along vibrating conveyor 22 become spaced apart from one another as they are deposited on high-speed conveyor 36 and accelerated from conveyor 22. The tackiness of the meat segments assists the belt of conveyor 36 in gripping each segment and pulling it away from vibrating conveyor 22 before another segment is ready to be deposited on conveyor 36. In this way, the adhesive characteristics of the meat segments assist in spacing the discrete segments on conveyor 36. Therefore, it is important to maintain the temperature of the segments above freezing, and preferably above about 40° F. so that they are sufficiently tacky when conveying the segments from conveyor 22 to conveyor 36.

The spaced meat segments are conveyed along high-speed conveyor 36, as designated by arrow 42, to a conventional inspection station 44. High-speed conveyor 36 stabilizes the segments as discussed above and accelerates them to a controlled speed before trajecting each segment into the air for inspection. At inspection station 44, at least one characteristic of each segment indicative of one of its components (e.g., lean or fat) is sensed. In response to the sensed characteristic(s), segments having a selected percentage of the component are separated from the remaining segments as discussed below. One suitable optical sorting system (including a suitable vibrating and belt conveyor), which has been used in conjunction with fruit and vegetables, is commercially available from Key Technology, Inc., Walla Walla, Wash. under the trademark COLORSORI ™.

The inspection station 44 includes sensors or cameras 46 and illuminators 48. The sensors and illuminators are arranged to illuminate and view the meat segments from underneath, as well as from the top, as they pass through the sensing zone 50. An air ejector 52, supplied with air through a source (not shown), is controlled by a control circuit (diagrammatically shown as 54) to selectively alter the trajectory or path of the meat segments 14 passing through sensing zone 50. Sensors 46 and ejectors 52 are coupled to control circuit 54 as is conventional in the art to operate air ejectors 52 in response to at least one sensed characteristic of the meat segments passing through sensing zone 50. Sensors 46, which are preferably photoelectric sensors, detect the presence of fat or lean meat, for example, in a respective meat segment and generate a signal representative of that component or the percentage of that component in the segment. The amount of fat or lean in any meat segment is proportional to the light value sensed with respect to the meat segment. The signal is then communicated to control circuit 54. The control circuit 54 is programmed to energize the ejectors such that meat segments having a selected percentage of a component such as lean or fat are sorted from the remaining segments. For example, control circuit 54 compares the received signals to the preselected ranges to determine the actuation of the ejectors by a microprocessor. Accordingly, segments of higher lean meat content can be separated from segments having a lower lean meat content. In this way, the invention provides a method and system for upgrading a given quantity of meat products which otherwise would be unsuitable for high-grade meat purposes such as hamburger and the like. The kind of meat on which the invention can be used would commonly be suitable for only low-quality, high-fat products. Such meat typically contains about half lean meat and half fat. The invention provides a method and system for upgrading these products to a fraction containing, for example, 75% lean meat and 25% fat which is a saleable meat product that can be further ground up and used for hamburger or other diverse meat products.

The above is a detailed description of a particular embodiment of the invention. It is recognized that departures from the disclosed embodiment may be made within the scope of the invention and that obvious modifications will occur to a person skilled in the art. The full scope of the invention is set out in the claims that follow and their equivalents. Accordingly, the claims and specification should not be construed to unduly narrow the full scope of protection to which the invention is entitled. For example, laser or electron beam detecting devices can be used in lieu of photoelectric sensors.

What is claimed is:

1. A process for separating selected components of meat products comprising the steps of:
   extruding meat product;
   cutting the extruded meat product to form a plurality of discrete pieces of material;
   conveying the discrete pieces to a sensor;
   maintaining the temperature of the meat product and discrete pieces of material above freezing during the extruding, cutting and conveying steps;
   sensing the presence of one of the selected components in each discrete piece of material conveyed to the sensor; and
   sorting the discrete pieces of material in response to the sensed component such that the discrete pieces having a selected percentage of the one of the selected components are separated from the remaining discrete pieces of material.

2. The process of claim 1 wherein the temperature of the meat product and discrete pieces of material is maintained above about 40° F. during the extruding, cutting and conveying steps.

3. The process of claim 1 wherein the temperature of the meat product and discrete pieces of material is maintained above freezing throughout the process.

4. The process of claim 1 further including the step of vibrating the discrete pieces of material immediately following the cutting step to substantially prevent the pieces from sticking together.

5. The process of claim 1 wherein the conveying step immediately follows the cutting step and comprises conveying the discrete pieces at a first speed along a first path to a second path where the pieces are conveyed to the sensor at a second speed that is substantially greater than the first speed, the discrete pieces are vibrated as they are conveyed along the first path to prevent the pieces from sticking together, and the change in speed of the segments from the first to second path being abrupt to space the segments from each other as they travel along the second path.

6. The process of claim 1 including the step of spacing the discrete pieces of material from each other before sensing the presence of one of the selected components.

7. The process of claim 6 wherein the discrete pieces are spaced about ¼ to 2 inches from each other before sensing the presence of one of the selected components.

8. The process of claim 6 wherein the discrete pieces are conveyed at a first speed along a first path to a second path where the pieces are conveyed at a second speed that is substantially greater than the first speed to effect the spacing among the pieces.

9. The process of claim 8 wherein the discrete pieces are vibrated as they are conveyed along the first path.

10. The process of claim 1 wherein the meat product is selected to include lean meat and fat components, and the sensing step comprises sensing the presence of one of the lean meat and fat components.

11. The process of claim 10 wherein the sorting step includes sorting the discrete pieces in response to the sensed component such that discrete pieces consisting essentially of fat are separated from the remaining discrete pieces of material.

12. The process of claim 10 wherein the sorting step comprises sorting the discrete pieces in response to the sensed component such that discrete pieces including at least a portion of lean meat are separated from the remaining discrete pieces of material.

13. The process of claim 1 wherein the cutting step includes cutting the extruded meat into pieces having a length of about ¼ to 1 inch.

14. The process of claim 13 wherein the cutting step includes forming the plurality of discrete pieces to have a length of about ½ inch.

15. The process of claim 13 wherein the extruding step includes forming the plurality of discrete pieces to have a rod shape and a transverse dimension of about ½ inch.

16. The process of claim 13 wherein the extruding step includes forming the plurality of discrete pieces to have a generally cylindrical shape and a diameter of about ½ inch.

17. The process of claim 1 wherein the extruding step includes forming the plurality of discrete pieces to have a rod shape and a transverse dimension of about ½ inch.

18. A method for processing meat product comprising the steps of:
    extruding meat product;
    cutting the extruded meat product at a cutting station to form discrete segments of material having lengths of about ¼ to 1 inch;
    feeding the segments from the cutting station directly to a vibrating conveyor immediately after the segments have been formed, and vibrating the segments along the vibrating conveyor to substantially prevent segments from clinging together;
    feeding the segments from the vibrating conveyor directly to a high-speed conveyor such that the segments undergo an abrupt increase in speed during the transition between the vibrating and high-speed conveyors which separates the segments from each other by at least about ¼ inch;
    passing the separated segments through the sensing zone of a sensor;
    sensing characteristics of the segments indicative of the presence of a component of the meat product; and
    sorting the segments in response to the sensed characteristics such that segments having a selected percentage of the component are separated from the remaining segments.

19. The method of claim 18 wherein the meat product is selected to include lean meat and fat components, and the sensing step comprises sensing the presence of characteristics of the segments indicative of the presence of the fat component.

20. The method of claim 18 wherein the meat product is selected to include lean meat and fat components, and the sorting step comprises sorting segments in response to the sensed characteristics such that segments having lean meat are separated from the remaining segments.

21. Apparatus for separating selected components of meat products comprising:
    means for extruding meat product containing a combination of components;
    means for cutting meat product which is extruded by the extruding means into segments;
    means for sensing characteristics of the meat product segments that are indicative of the segment components;
    first and second conveyors for conveying the meat product segments to said sensing means, said first conveyor being a vibrating conveyor that is positioned beneath and vertically spaced from said cutting means, said second conveyor being located downstream from said first conveyor and positioned for receiving meat segments from the first conveyor and conveying the segments to said sensing means; and
    means responsive to said sensing means for sorting the meat product segments according to the sensed components.

22. The apparatus of claim 21 wherein said second conveyor includes means for conveying the meat segments about 400 to 600 ft/min.

23. The apparatus of claim 21 wherein the upstream portion of said second conveyor is positioned beneath and vertically spaced from said first conveyor.

24. The process of claim 1 wherein the meat product is cut as extruded.

25. The process of claim 24 wherein the from of the discrete pieces is maintained substantially the same throughout the conveying, sensing and sorting steps.

26. A process for separating selected components of meat products comprising the steps of:
    extruding meat product;
    cutting the extruded meat product to form a plurality of discrete pieces of material;
    conveying the discrete pieces to a sensor;
    vibrating the discrete pieces of material during the conveying step to substantially prevent the pieces from sticking together;
    maintaining the temperature of the meat product and discrete pieces of material above freezing during the extruding, cutting and conveying steps;
    sensing the presence of one of the selected components in each discrete piece of material conveyed to the sensor; and
    sorting the discrete pieces of material in response to the sensed component such that the discrete pieces having a selected percentage of the one of the selected components are separated from the remaining discrete pieces of material.

27. The process of claim 26 wherein the discrete pieces of material are transferred directly to a vibrating conveyor after the cutting step.

28. A process for separating selected components of meat products comprising the steps of:
    extruding meat product;
    cutting the extruded meat product to form a plurality of discrete pieces of material;
    conveying the discrete pieces along a first path immediately following the cutting step, the pieces being conveyed at a first speed along the first path to a second path where the pieces are conveyed to a sensor at a second speed that is substantially greater than the first speed, the discrete pieces being vibrated as they are conveyed along the first path to substantially prevent the pieces from sticking together, and the change in speed of the segments from the first to second path being abrupt to space the segments from each other as they travel along the second path;
    maintaining the temperature of the meat product and discrete pieces of material above freezing during the extruding, cutting and conveying steps;
    sensing the presence of one of the selected components in each discrete piece of material conveyed to the sensor; and
    sorting the discrete pieces of material in response to the sensed component such that the discrete pieces having a selected percentage of the one of the selected components are separated from the remaining discrete pieces of material.

* * * * *